United States Patent
Lakshmi et al.

(10) Patent No.: US 11,382,945 B2
(45) Date of Patent: Jul. 12, 2022

(54) POLYHERBAL COMPOSITION FOR PREVENTING AND ALLEVIATING POLYCYSTIC OVARY SYNDROME

(71) Applicant: SRM INSTITUTE OF SCIENCE AND TECHNOLOGY, Chennai (IN)

(72) Inventors: Karunanidhi Santhana Lakshmi, Chennai (IN); Marakanam Srinivasan Uma Shankar, Guduvanchery (IN); Vellapandian Chitra, Kancheepuram (IN); Mohan Sumithra, Guduvanchery (IN); Thangavel Mahalingam Vijaya Kumar, Kancheepuram (IN)

(73) Assignee: SRM INSTITUTE OF SCIENCE AND TECHNOLOGY, Chennai (IN)

(*) Notice: Subject to any disclaimer, the term of this patent is extended or adjusted under 35 U.S.C. 154(b) by 114 days.

(21) Appl. No.: 16/448,298

(22) Filed: Jun. 21, 2019

(65) Prior Publication Data

US 2020/0397841 A1    Dec. 24, 2020

(51) Int. Cl.
| | |
|---|---|
| *A61K 36/484* | (2006.01) |
| *A61K 47/46* | (2006.01) |
| *A61K 36/38* | (2006.01) |
| *A61K 36/53* | (2006.01) |
| *A61K 36/736* | (2006.01) |
| *A61K 36/899* | (2006.01) |
| *A61K 36/81* | (2006.01) |
| *A61K 36/55* | (2006.01) |
| *A61K 36/906* | (2006.01) |
| *A61K 31/7004* | (2006.01) |
| *A61K 9/00* | (2006.01) |
| *A61K 9/28* | (2006.01) |
| *A61K 9/20* | (2006.01) |
| *A61K 9/48* | (2006.01) |
| *A61K 36/23* | (2006.01) |

(52) U.S. Cl.
CPC .......... *A61K 36/484* (2013.01); *A61K 9/0056* (2013.01); *A61K 9/2018* (2013.01); *A61K 9/2095* (2013.01); *A61K 9/2833* (2013.01); *A61K 9/4808* (2013.01); *A61K 31/7004* (2013.01); *A61K 36/23* (2013.01); *A61K 36/38* (2013.01); *A61K 36/53* (2013.01); *A61K 36/55* (2013.01); *A61K 36/736* (2013.01); *A61K 36/81* (2013.01); *A61K 36/899* (2013.01); *A61K 36/906* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 2006/0159773 A1* | 7/2006 | Stephen | |
| 2006/0246163 A1* | 11/2006 | Tae-Lin | |
| 2014/0271923 A1* | 9/2014 | Brian | |
| 2019/0054088 A1* | 2/2019 | Jayanthy | |

FOREIGN PATENT DOCUMENTS

CN    103597071 A  *  2/2014  ........... A61K 31/198

OTHER PUBLICATIONS

Welankiwar (Review: Tablet coating process, https://www.pharmatutor.org/articles/review-tablet-coating-process), Apr. 5, 2013 (Year: 2013).*
CN-103597071-A translated (Year: 2014).*

* cited by examiner

*Primary Examiner* — Susan Hoffman
*Assistant Examiner* — Jacob A Boeckelman
(74) *Attorney, Agent, or Firm* — The Roy Gross Law Firm, LLC; Roy Gross

(57) ABSTRACT

The present disclosure provides a polyherbal composition for preventing and alleviating Polycystic ovary syndrome. The composition comprises an insulin regulator selected from *Cinnamomum zeylyanicum* and *Trigonella foenum*, a blood sugar regulator selected from *Garcinea cambogia* and *Emblica officinalis*, a cholesterol lowering agent selected from *Linum usittatissimum* and *Tribulus terrestris*, a prolactin regulator selected from *Vitex agnus-castus* and *Trachyspermum ammi*, a cyst shrinking component selected from *Zingiber officinale* and *Putranjiva roxburghii*, an androgen regulator selected from *Ocimum sanctum*, *Glycyrrhiza glabra* and *Mentha spicate*, an adrenal gland regulator selected from *Withania somnifera* and *Sesamum indicum*, an inositol containing component selected from *Oryza sativa* and *Cicer arietinum*, a binder selected from *Ferula foetida* and *Prunus amygdalus* along with a pharmaceutically acceptable excipient.

8 Claims, 6 Drawing Sheets

POLYHERBAL COMPOSITION FOR PREVENTING AND ALLEVIATING POLYCYSTIC OVARY SYNDROME

FIELD OF THE INVENTION

The present disclosure relates to a polyherbal composition for preventing and alleviating polycystic ovary syndrome.

Definitions

As used in the present disclosure, the following terms are generally intended to have the meaning as set forth below, except to the extent that the context in which they are used indicate otherwise.

Polyherbal composition: The term "polyherbal composition" refers to a composition containing a synergistic blend of different herbs along with pharmaceutically acceptable ingredients.

Plant ingredients: The term "plant ingredients" refers to powdered plant parts and/or plant extracts of different herbs.

Polycystic ovary syndrome (PCOS): The term "Polycystic ovary syndrome (PCOS)", refers to a condition with complex genetic, endocrine and metabolic abnormalities, diagnostically characterized by anovulation.

Pharmaceutical unit: The term "pharmaceutical unit" refers to a fixed amount of the polyherbal composition present in the form of a chewable lozenge tablet, a sugar coated oral tablet, a polymer film coated tablet, a gelatin shell encapsulated tablet, a sachet, a bubble bag, an herbal dip bag, syrup, jelly or elixir.

BACKGROUND OF THE INVENTION

The background information herein below relates to the present disclosure but is not necessarily prior art.

Polycystic ovary syndrome (PCOS), a condition that afflicts women of reproductive age, is a complex genetic, endocrine and metabolic abnormalities, diagnostically characterized by anovulation. Hormonally, the disease may be characterized by an elevation in serum androgens. A condition of hyperandrogenism is usually observed, which triggers an excessive acyclic estrone production that, in its turn, determines a gonadotropin hyper production, mainly Luteinizing hormone, hereinafter referred to as LH. The imbalance in the ratio of Luteinizing hormone/Follicle Stimulating hormone (FSH) reduces follicular maturation, resulting in anovulation and hyper stimulation of theca cells, with androgen hyper production. Concomitantly, in the presence of PCOS, a reduced conversion of androgens into estrogens at level of granulose cells occurs, determining an androgen accumulation which induces follicular maturation regression or chronic follicular atresia.

Most commonly, females suffering from PCOS exhibit irregular menstrual cycles and menstrual irregularities such as oligomenorrhoea, amenorrhoea, metrorrhagia, infertility. Further, in some cases, hyperandrogenism commonly manifests itself with hirsutism, seborrhea which is due related to an excessive stimulation of sebaceous glands due to high androgen concentrations, acne which is due to occlusion of pores in the skin with inflammation and pus formation and alopecia. In some cases, women suffer from PCOS related obesity, frequently associated with a condition of hyperinsulinism related to insulin-resistance. It has been observed that insulin-resistance plays a key role in the genesis of this syndrome in 33% of lean women with PCOS. The most frequently reported insulin-resistance-related metabolic disorders include changes in the lipid profile, reduced glucose tolerance or type-2 diabetes mellitus, hyperfibrinogemia and fibrinolytic defects, arterial hypertension.

First-line treatment of PCOS is usually the oral contraceptive pill (OCP) for women in whom fertility is not immediately desired. Anti-androgen therapy is also used as method of treating PCOS. One such example of anti-androgen therapy is an oestroprogestinic therapy, wherein there is a combination of estrogens with a progestin possessing antiandrogenic properties, in order to regulate the menstrual cycle and reduce hyperandrogenism signs. However, one significant drawback of the use of the oestroprogestinic therapy is that if the patient is trying to become pregnant, ovulation should be induced by discontinuation of estrogen/progestin drugs or by administration of an estrogen supplement with weak activity, such as clomiphene, acting also as antiestrogen. This can lead to important undesirable effects, such as hot flushes, changes in some blood components and visual disturbances, also of significant nature.

Yet another method of treating PCOS, is the administration of Follicle Stimulating Hormone, hereinafter referred to as FSH. The FSH is a hormone acting on follicles in the last step of their maturation process and is used to counter the effects of PCOS. However, FSH use may lead to superovulation phenomena. In addition, excessive FSH doses may cause multiple ovulations and the ovarian hyper stimulation syndrome, a condition characterized by an increased vascular permeability, with fluid transfer to the extracellular compartment and consequent hypovolemia, haemoconcentration and concomitantly ascites, pleural and pericardial effusions. The use of these chemical methods often result in varied side effects including but not limited to the risk of potentially harmful electrolyte imbalance, induction chemical menopause leading to add-back hormonal therapy.

Additionally, a therapeutic alternative to the hormonal treatment is the hypoglycaemic therapy. In hypoglycaemic therapy oral hypoglycaemic agents is administered to patients which aims to reduce the correlations between hyperinsulinemia and hormonal metabolic changes. However, the major limitation of this type of is that being a long-term treatment, the hypoglycemic therapy impairs the pancreatic function.

To summarize, hormonal therapy has some serious side effects in the normal functioning and undesirable effects such as hot flushes, changes in some blood components and visual disturbances, potentially harmful electrolyte imbalance, induction chemical menopause leading to add-back hormonal therapy, whereas hypoglycemic therapy leads to impairment of pancreatic function.

Pre-emptive measures taken to avoid PCOS are also commonly adopted in the presence of risk factors such as prepubertal and/or early pubertal hypertrichosis and overweight. These measures include a restriction of the calorie intake from the diet and increased physical activity. However, in some cases despite the pre-emptive measures taken, occurrences of PCOS can still be seen.

Hence, to circumvent the drawbacks caused by the above cited therapy methods, there is felt a need which not only helps in curing PCOS but is also helpful in prevention of developing PCOS without altering the regular diets or manifesting any side effects.

OBJECTS OF THE INVENTION

Some of the objects of the present disclosure, which at least one embodiment herein satisfies, are as follows:

It is an object of the present disclosure to ameliorate one or more problems of the prior art or to at least provide a useful alternative.

An object of the present disclosure is to provide a polyherbal composition for preventing and alleviating polycystic ovary syndrome.

Another object of the disclosure is to provide a method of preparing the polyherbal composition for preventing and alleviating polycystic ovary syndrome.

Other objects and advantages of the present disclosure will be more apparent from the following description, which is not intended to limit the scope of the present disclosure.

SUMMARY OF THE INVENTION

One aspect of the present disclosure provides a polyherbal composition for preventing and alleviating polycystic ovary syndrome. The composition comprises an insulin regulator selected from *Cinnamomum zeylyanicum* and *Trigonella foenum*, a blood sugar regulator selected from *Garcinea cambogia* and *Emblica officinalis*, a cholesterol lowering agent selected from *Linum usittatissimum* and *Tribulus terrestris*, a prolactin regulator selected from *Vitex agnus-castus* and *Trachyspermum ammi*, a cyst shrinking component selected from *Zingiber officinale* and *Putranjiva roxburghii*, an androgen regulator selected from *Ocimum sanctum*, *Glycyrrhiza glabra* and *Mentha spicate*, an adrenal gland regulator selected from *Withania somnifera* and *Sesamum indicum*, an inositol containing component selected from *Oryza sativa* and *Cicer arietinum*, a binder selected from *Ferula foetida* and *Prunus amygdalus* along with a pharmaceutically acceptable excipient. The insulin regulator is present in an amount ranging from 15% w/w to 25% w/w. The blood sugar regulator is present in an amount ranging from 15% w/w to 20% w/w. The cholesterol lowering agent is present in an amount ranging from 10% w/w to 15% w/w. The prolactin regulator is present in an amount ranging from 3% w/w to 7% w/w. The cyst shrinking component is present in an amount ranging from 10% w/w to 15% w/w. The androgen regulator is present in an amount ranging from 2% w/w to 12% w/w. The adrenal gland regulator is present in an amount ranging from 10% w/w to 15% w/w. The inositol containing component is present in an amount ranging from 1% w/w to 10% w/w. The binder is present in an amount ranging from 1% w/w to 5% w/w. The pharmaceutically acceptable excipient is present in an amount ranging from 1% w/w to 5% w/w.

The composition in a pharmaceutically acceptable form is used for alleviating PCOS when administered in acceptable dosage ranges.

BRIEF DESCRIPTION OF THE ACCOMPANYING DRAWING

The method of the present disclosure will now be described with the help of the accompanying drawing, in which.

DETAILED DESCRIPTION OF THE INVENTION

Figure 1:
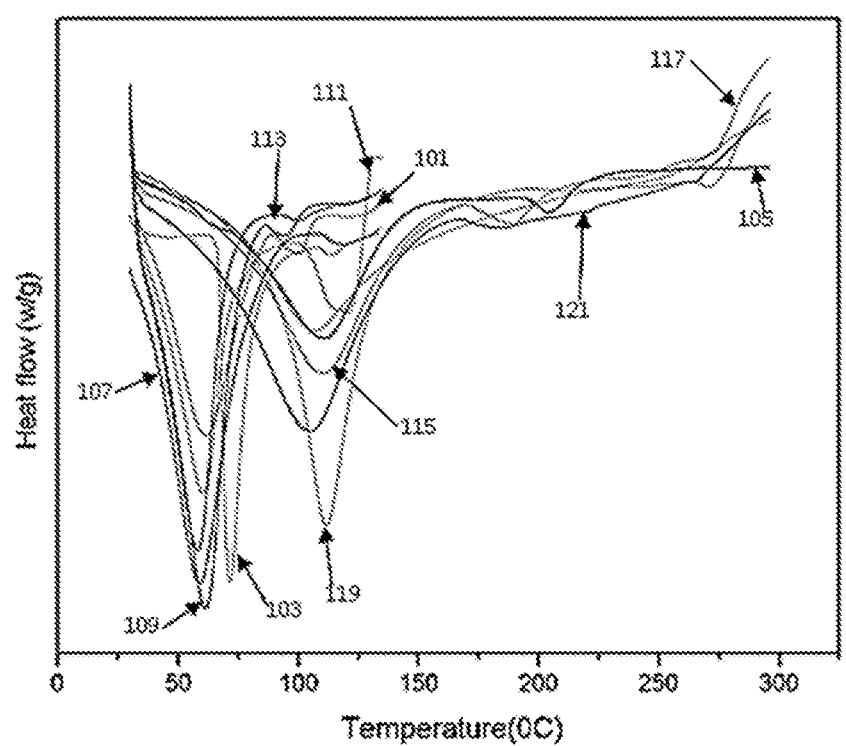
FIG. 1 illustrates DSC spectroscopy studies of the polyherbal composition FI, according to an embodiment of the disclosure.

Embodiments, of the present disclosure, will now be described with reference to the accompanying drawing.

Embodiments are provided so as to thoroughly and fully convey the scope of the present disclosure to the person skilled in the art. Numerous details are set forth, relating to specific ingredients, and methods, to provide a complete understanding of embodiments of the present disclosure. It will be apparent to the person skilled in the art that the details provided in the embodiments should not be construed to limit the scope of the present disclosure. In some embodiments, well-known processes and well-known techniques are not described in detail.

The terminology used in the present disclosure is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, steps, elements, and/or constituents, but do not forbid the presence or addition of one or more other features, steps, elements, constituents, ingredients and/or groups thereof. The particular order of steps disclosed in the method/process of the present disclosure is not to be construed as necessarily requiring their performance as described or illustrated. It is also to be understood that additional or alternative steps may be employed.

As used herein, the term "and/or" includes any and all combinations of one or more of the associated listed elements.

One aspect of the present disclosure provides a polyherbal composition for preventing and alleviating polycystic ovary syndrome, hereinafter referred to as PCOS. The polyherbal composition is a synergistic blend of different plant parts and/or plant extracts of different herbs having preventive and curative action against PCOS. The polyherbal composition comprises an insulin regulator, a blood sugar regulator, a cholesterol lowering agent, a prolactin regulator, a cyst shrinking component, an androgen regulator, an adrenal modulator, an inositol containing component, a binder, and a pharmaceutically acceptable excipient.

The insulin regulator is selected from plant parts and/or plant extracts of *Cinnamomum zeylyanicum* and *Trigonella foenum*. The insulin regulator is present in the range of 15% w/w to 25% w/w.

The blood sugar regulator is selected from plant parts and/or plant extracts of *Garcinea cambogia* and *Emblica officinalis*. The blood sugar regulator is present in the range of 15% w/w to 20% w/w.

The cholesterol lowering agent is selected from plant parts and/or plant extracts of *Linum usittatissimum* and *Tribulus terrestris*. The cholesterol lowering agent is present in the range of 10% w/w to 15% w/w.

The prolactin regulator is selected from plant parts and/or plant extracts of *Vitex agnus-castus*, and *Trachyspermum ammi*. The prolactin regulator is present in the range of 3% w/w to 7% w/w.

The cyst shrinking component is selected from plant parts and/or plant extracts of *Zingiber officinale* and *Putranjiva roxburghii*. The cyst shrinking component is present in the range of 10% w/w to 15% w/w.

The androgen regulator is selected from plant parts and/or plant extracts of *Ocimum sanctum, Glycyrrhiza glabra* and *Mentha spicate*. The androgen regulator is present in the range of 2% w/w to 12% w/w.

The adrenal gland regulator is selected from plant parts and/or plant extracts of *Withania somnifera* and *Sesamum indicum*. The adrenal modulator is present in the range of 10% w/w to 15% w/w.

The inositol containing component is selected from plant parts and/or plant extracts of *Oryza sativa* and *Cicer arietinum*. The composition contains inositol in one or more of its isomeric forms or salts in an amount ranging from 1% w/w to 10% w/w.

Inositol component present in the composition helps in increasing insulin action by improving cell sensitivity to insulin. Inositol plays an important role as the structural basis for a number of secondary messengers including synthesis of phosphatidyl inositol 3-kinase (PI 3-kinase), a key messenger to improve insulin sensitivity and thereby reducing insulin resistance. Inositol corrects the impaired insulin pathway and reduce the signs and symptoms of insulin resistance. Inositol is also a part of vitamin B complex.

Inositol inhibits adenyl cyclase, thus reducing the release of free fatty acids from adipose tissues. Inositol also helps in regulating body weight, systolic and diastolic blood pressure, total plasma cholesterol and triglyceride concentrations. Inositol concentration in the follicular fluid improves oocyte quality. Locally, intrafollicular presence of inositol helps in increased thecal androgen production thereby alleviating much of the metabolic dysregulation of PCOS.

The binder is selected from plant parts and/or plant extracts of *Ferula foetida* and *Prunus amygdalus*. The binder is present in the range of 1% w/w to 5% w/w. The plant parts and/or plant extracts of *Ferula foetida* and *Prunus amygdalus* used as binder not only help in promoting cohesiveness while formulating the polyherbal composition as a tablet but also play a role in alleviating symptoms of polycystic ovary syndrome. *Ferula foetida* and *Prunus amygdalus* helps in achieving hormonal balance, reduce acne, regulating blood pressure, regulates blood cholesterol level and acts as an effective antioxidant.

The different herbs as disclosed above have been procured commercially from a local herbal grocery store in Tamil Nadu, India.

The pharmaceutically acceptable excipient is selected from the group consisting of an edible carrier, a binder, a diluent, a disintegrating agent, a coloring agent, a stabilizer, an emulsifier, a film-forming agent, a plasticizer, a wetting agent, a thickener, a lubricant, a preservative agent, a sweetening agent, a flavoring agent and combinations thereof.

The edible carrier is selected from the group consisting of water, fatty oil, glycol, oil, alcohol, microcrystalline cellulose and combinations thereof.

The binder is selected from the group consisting of dry starch, gelatin, acacia gum, tragacanth gum, almond gum, sucrose, polyethylene glycol, sucrose syrup, mucilage of starch, and polyvinyl pyrolidine in isopropyl alcohol.

The diluent is selected from the group consisting of dextrose, anhydrous lactose, spray dried lactose, mannitol, microcrystalline cellulose, starch, sucrose, di or tri-calcium phosphate, calcium carbonate and combinations thereof.

The disintegrating is selected from the group consisting of maize starch, potato starch, alginic acid, microcrystalline cellulose, guar gum, sodium starch glycolate, hydroxyl propyl methyl cellulose, methyl cellulose, sodium carboxy methyl cellulose and combinations thereof.

The coloring agent is selected from the group consisting of chlorophyll, anthocyanins, caramel, caroteinoids, annatto, saffron, betanin, turmeric, canthaxanthin, riboflavin and combinations thereof.

The stabilizer is selected from the group consisting of methyl paraben, propyl paraben, sodium benzoate, citric acid, sodium citrate and combinations thereof.

The emulsifier is selected from the group consisting of mustard, soy and egg lecithin, monoglycerides, diglycerides, polysorbates, carrageenan, guar gum, canola oil and combinations thereof.

The film-forming agent is selected from the group consisting of shellac, cellulose acetate phthalate, hydroxypropyl methyl cellulose phthalate, amino ethyl methacrylate, polyvinyl acetate, phthalate ethyl cellulose, methyl hydroxyethyl cellulose, hydroxy ethyl cellulose, hydroxypropyl methyl cellulose, sodium hydroxyl methyl cellulose, hydroxyl ethyl cellulose and hydroxyl methyl cellulose, polyethylene glycol and polyvinyl pyrollidine and combinations thereof.

The plasticizer is selected from the group consisting of mineral oil, glycerin, propylene glycol and combinations thereof.

The wetting agent is selected from the group consisting of bentonite, alginates, cellulose, tragacanth and combinations thereof.

The thickener is selected from the group consisting of methyl cellulose, acacia, tragacanth, gelatin and combinations thereof.

The lubricating agent is selected from the group consisting of purified talc, calcium stearate, magnesium stearate and combinations thereof.

The preservative agent is selected from the group consisting of sodium benzoate, sodium citrate, peppermint water, essential oils and combinations thereof.

The sweetening agent is selected from the group consisting of *stevia*, xylose, ribose, glucose, mannose, galactose, fructose, dextrose, sucrose, lactose, maltose, saccharin, partially hydrolyzed starch, corn syrup, and sugar alcohols such as sorbitol, xylitol, mannitol, glycerin and combinations thereof.

The flavoring agent is selected from the group consisting of natural and artificial flavors of peppermint, menthol, cinnamon, vanilla, cherry, grape, orange, strawberry and combinations thereof.

The polyherbal composition further comprises one or more vitamins including B-complex vitamins, vitamin A, and vitamin C. Preferred B complex vitamins are selected from niacin, vitamin B6, vitamin B8, vitamin B9 vitamin B12, and combinations thereof.

The polyherbal composition also comprises one or more minerals salts of Mg, K, Na, Zn, Fe, Cr, Se, and Mn.

The plant ingredients are taken in different proportions, along with a pharmaceutically acceptable excipient to formulate it into a pharmaceutical unit. The different proportions are determined depending upon the severity of polycystic ovary syndrome and its related symptoms, condition, any further treatment in progress, the individual's health and the response to the composition. The total amount of the plant ingredients, can vary from 1 g to 3 g per pharmaceutical unit.

The physical form of the pharmaceutical unit is either solid, liquid or a semi solid. In the solid form, the pharmaceutical unit is a chewable lozenge tablet, a sugar coated oral tablet, a polymer film coated tablet, a hard gelatin encapsulated tablet, a soft gelatin encapsulated tablet. In the solid form, the pharmaceutical unit can also be a sachet, a bubble bag or an herbal dip bag containing predetermined amounts the plant ingredients. When the pharmaceutical unit is sachet or bag type, the constituents of the pharmaceutical unit is mixed with hot water and consumed as a health drink. When the pharmaceutical unit is an herbal dip bag type, the herbal dip bag is dipped into hot water and consumed as a polyherbal infusion.

In one embodiment of the disclosure, the pharmaceutical unit is a tablet. The acceptable dosage regimen for a tablet is 3 tablets/per day, until the PCOS manifestations get subsided. The pharmaceutical unit in the tablet form is formulated in a manner such that there is sustained release of the plant ingredients.

In an embodiment of the disclosure, wherein the pharmaceutical unit passes through the upper part of the gastrointestinal tract, the pharmaceutical unit is coated with an enteric coating to prevent breakdown in the upper part of the gastrointestinal tract.

In the solid form, the plant ingredients are combined with excipients such suitable edible carriers, binders, diluents, disintegrating agents, coloring agents, fillers, stabilizers, emulsifiers, film-forming agents, plasticizers, wetting agents, thickeners, lubricants and sweetening agents.

In an embodiment of the disclosure, the edible carrier is selected from the group including starches, sugars, microcrystalline cellulose and combinations thereof.

In the liquid form, the pharmaceutical unit is a polyherbal syrup or a polyherbal smoothie health drink.

In the liquid form, the plant ingredients are combined with suitable liquid carrier, a coloring agent, a flavoring agent, a preservative and a sweetening agent. The liquid carrier is selected from water, fatty oil, glycol, oil, alcohol and combinations thereof.

In the semi-solid form, the pharmaceutical unit of the polyherbal composition is in the form of a jelly.

In one embodiment of the disclosure, the polyherbal composition comprises powdered plant parts of different herbs. The polyherbal composition comprises 15% w/w to 25% w/w of *Cinnamomum zeylyanicum* powdered bark; 10% w/w to 15% w/w of *Linum usittatissimum* powdered seeds; 3% w/w to 7% w/w of *Vitex agnus-castus* dried berries powder, 10% w/w to 15% w/w of *Zingiber officinale* powdered rhizome; 2% w/w to 12% w/w of *Ocimum sanctum* powdered leaves; 15% w/w to 20% w/w of *Emblica officinalis* dried berries powder, 2% w/w to 12% w/w of *Mentha spicate* powdered leaves; 10% w/w to 15% w/w of *Withania somnifera* powdered root; 11% w/w to 5% w/w of *Ferula foetida* powdered resin; and 1% w/w to 10% w/w of *Cicer arietinum* powdered legume.

In another embodiment of the disclosure, the polyherbal composition comprises 15% w/w to 25% w/w of *Trigonella foenum* powdered seeds; 10% w/w to 15% w/w of *Tribulus terrestris* powdered seeds; 3% w/w to 7% w/w of *Trachyspermum ammi* powdered seeds; 10% w/w to 15% w/w of *Putranjiva roxburghii* powdered seeds; 2% w/w to 12% w/w of *Glycyrrhiza glabra* powdered roots; 5% w/w to 20% w/w of *Garcinea cambogia* dried fruits powder; 2% w/w to 12% w/w of *Ocimum sanctum* powdered seeds; 10% w/w to 15% w/w of *Sesamum indicum* powdered seeds; 1% w/w to 5% w/w of *Prunus amygdalus* dried gum powder; and 1% w/w to 10% w/w of *Oryza sativa* grain powder.

The mixture of the powdered plant parts, hereinafter referred to as primary mixture, is then subjected to pre-formulation studies for evaluating various parameters such as physical appearance, particle size distribution, loss on drying, Loose Bulk Density (LBD), Tapped bulk density (TBD), apparent density, true density, Hausner ratio and Carr's Compressibility index. The pre-formulation studies are carried out so as to obtain uniform weight necessary for formulating the composition into pharmaceutically acceptable forms.

Pre-Formulation Studies

1. Physical appearance: Color of the primary mixture is brownish.

2. Particle Size distribution: The particle size distribution of the primary mixture is evaluated by sieve analysis using standard sieves of sieve size 80.

3. Loss on drying: To calculate loss on drying, a predetermined amount of the primary mixture is transferred into a dried, glass stoppered shallow weighing bottle. The contents are distributed evenly and placed in the drying chamber. The stopper is removed from the bottle and the contents is dried for a specified time to achieve a constant weight. The loss on drying is calculated using the following formula:

$$\text{Loss on drying (\%)} = [(\text{Initial weight} - \text{Final weight})/(\text{Initial weight})] \times 100$$

4. Loose Bulk Density (LBD): The Loose bulk density is determined by pouring a weighed quantity of the primary mixture into graduated cylinder and measuring the volume and weight. The loose bulk density is calculated using the following formula:

$$\text{LBD} = \text{Weight of the primary mixture/volume of the packing.}$$

5. Tapped bulk density (TBD): To calculate the tapped bulk density, a pre-determined amount of the primary mixture is placed in a graduated cylinder. The cylinder is allowed to fall under its own weight on to a hard surface from a predetermined height at two second intervals. The tapping is continued until no further change in volume is noted. The tapped bulk density is calculated using the following formula.

$$\text{TBD} = \text{Weight of the primary mixture/volume of the tapped packing}$$

6. Apparent bulk density: To calculate the Apparent bulk density, a pre-determined amount of the primary mixture is introduced into a dry cylinder, without compacting. The primary mixture is carefully leveled without compacting and the unsettled apparent volume, Vo, is read. The bulk density is calculated using the following formula.

$$\rho b = M/Vo$$

Wherein, $\rho b$ = Apparent bulk density, M = Weight of sample, V = Apparent volume of primary mixture.

7. True density (Dt): The true density of the primary mixture is determined using the specific gravity bottle method. True density (Dt) is calculated using the following equation:

$$Dt = wa + w - b \times SG,$$

where w is the weight of powder, a is weight of bottle+dd water; b is weight of bottle+dd water+powder, and SG is specific gravity of dd water.

8. Hausner ratio: It is the measurement of frictional resistance of the primary mixture. It is determined by using the following formula Hausner ratio=TBD/LBD The ideal range for the primary mixture is in the range of 1.2-1.5.

9. Carr's Compressibility index: The Compressibility index of the blends is determined by Carr's compressibility index.

Compressibility index (%)=(TBD−LBD)×100/TBD

10. Angle of repose: Angle of repose is determined by using funnel method and is calculated using the following equation:

Tan θ=$h/r$

Where, h=height of primary mixture
r=radius of the primary mixture cone formed

In another aspect, the disclosure provides a method of preparation of the polyherbal composition.

In one embodiment of the disclosure, wherein the polyherbal composition is a pharmaceutical unit in the form of oral tablets the method of preparation comprises the initial steps of passing the powdered fraction of the various plant parts and the excipients through a sieve of size 22 to obtain granules. The granules are further subjected to either wet granulation technique, dry granulation technique and direct compression techniques to obtain the pharmaceutical unit.

The formulated pharmaceutical unit is then studied for organoleptic properties, diameter and thickness, weight variation, friability and hardness.

a. Weight variation test: The average weight is determined by randomly selecting and weighing the pharmaceutical units. Each pharmaceutical unit is also weighed individually. The deviation from the average weight in each case is calculated and expressed as a percentage. Not more than two of the pharmaceutical unit from the sample size deviate from the average weight by a greater percentage and none of the pharmaceutical unit deviate by more than double that percentage.

b. Percentage friability test: The friability of the pharmaceutical unit is determined by Roche friabilator. Percentage of weight loss of randomly selected pharmaceutical unit from each batch is tumbled in a friability tester. After 4 minutes of rotating at 25 rpm, the dust of the pharmaceutical unit is removed, and the percentage of weight loss is calculated using the formula.

Percentage friability test=Initial weight−final weight/initial weight×100 c. Hardness test: A pharmaceutical unit requires a certain amount of strength or hardness and resistance friability to withstand mechanical shocks of handling in all processes. The hardness of randomly selected pharmaceutical units is determined by the Pfizer hardness tester.

The polyherbal composition of the present disclosure is an effective therapeutic alternative to conventionally known hormonal therapies. Conventional pharmaceutical management is limited by the prevalence of contraindications in women with PCOS, non-effectiveness and side-effects and preferences for alternatives to pharmaceutical management.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Experiment-1: Preparation of Polyherbal Composition for Preventing and Alleviating Polycystic Ovary Syndrome The polyherbal composition in the form of a tablet was prepared by direct compression method.

Powdered solid fraction of the following components were taken in quantities as illustrated in table 1

TABLE 1

| Ingredients | Quantity (Per 3 g of tablet) |
| --- | --- |
| *Cinnamomum zeylyanicum* bark | 0.66 g |
| *Linum usittatissimum* seeds | 0.33 g |
| *Vitex agnus-castus* berries | 0.16 g |
| *Zingiber officinale* rhizome | 0.33 g |
| *Ocimum sanctum* leaves | 0.33 g |
| *Emblica officinalis* berries | 0.5 g |
| *Mentha spicate* leaves | 0.06 g |
| *Withania somnifera* roots | 0.33 g |
| *Ferula foetida* resin | 0.1 g |
| *Cicer arietinum* legume | 0.16 g |
| Total | 2.96 g |

The combination of above ingredients was referred to as Formula I (FI). The above ingredients were mixed together to obtain a primary mixture. Pre-formulation studies were carried out for a total of 9 g of primary mixture. The different properties of the mixture are provided in the table 2 below:

TABLE 2

| S. No. | Evaluations | Observations |
| --- | --- | --- |
| 1 | Physical appearance | Brownish color |
| 2 | Fineness | 25.22% |
| 3 | Loss on drying | 0.9% |
| 4 | Loose Bulk density | 0.415 gm/cc |
| 5 | Tapped Bulk density | 0.5496 gm/cc |
| 6 | Apparent density | 7.807 gm/cc |
| 7 | True density | 1.705 gm/cc |
| 8 | Hausner's ratio | 1.322 |
| 9 | Carr's Compressibility index | 24.408 |
| 10 | Angle of repose | 24 |

The primary mixture along with 60 mg almond gum as binder, 5 mg of magnesium stearate as lubricant, and 5 mg of talc as glidant were taken and passed through sieves of size no. 80 to obtain a secondary mixture. After sieving, the secondary mixture was subjected to a final round of mixing in a blender to obtain a powder blend of the herbal ingredients.

The tablets were made by direct compression using the powder blends on a rotating tablet presses using 11×8 mm punch set with appropriate compression pressure and the die cavity was adjusted for required weight. The obtained tablets were compressed to 3000 mg tablets. The tablets were evaluated for organoleptic properties, diameter and thickness, weight variation, friability and hardness.

Thickness of the tablet: The tablet thickness was calculated by Vernier calipers. Tablet was put in between two jaws vertically and measured thickness and 6 tablets were used for this test and expressed in mm.

Weight variation test: The average weight was determined by randomly selecting and weighing 20 tablets. Each tablet was also weighed individually. The deviation from the average weight in each case was calculated and expressed as a percentage. Not more than two of the tablets from the sample size deviate from the average weight by a greater percentage and none of the tablets deviate by more than double that percentage.

Percentage friability test: The friability of tablets was determined by Roche friabilator. Percentage of weight loss of 20 tablets randomly selected from each batch tumbled in friability apparatus. After 4 minutes of rotating at 25 rpm, the dust of tablets was removed, and the percentage of weight loss was calculated using the formula.

Percentage friability test=Initial weight–final weight/
initial weight×100

Hardness test: Tablet requires a certain amount of strength or hardness and resistance friability to withstand mechanical shocks of handling in all processes. The hardness of randomly selected 20 tablets of each composition was determined by the Pfizer hardness tester. It is measured in kg/inch$^2$.

Disintegration test: The disintegration time of tablets was determined using the digital microprocessor based disintegration test apparatus. One tablet was introduced into each tube and added a disc. The assembly was suspended in a 1000 mL beaker filled in with water. The volume of water was such that the wires mesh at its highest point (at least 25 mm) below the surface of the water, and at its lower point (at least 25 mm) above the bottom of the beaker. The apparatus was operated and maintained at 37±2° C. The time requires to all tablets to disintegrate and pass through wire mesh was noted.

The results of the test are summarized in the table 3 below.

TABLE 3

| S. No. | Evaluations | Observations |
| --- | --- | --- |
| 1 | Physical appearance | Brownish color |
| 2 | Thickness of tablets | 1.12 ± 0.01 cm |
| 3 | Weight variation | 3000 mg ± 1 mg per tablet weight |
| 4 | Friability | 0.55% |
| 5 | Hardness | 23 kg/cm$^2$ |
| 6 | Disintegration Time required for complete chewing | 5-10 mins. |

Experiment-2: Preparation of Polyherbal Composition for Preventing and Alleviating Polycystic Ovary Syndrome In the second example, the powdered fraction of the following components was taken in quantities as illustrated below table 4:

TABLE 4

| Ingredients | Quantity (Per 3 g of tablet) |
| --- | --- |
| Trigonella foenum seeds | 0.66 g |
| Tribulus terrestris seeds | 0.33 g |
| Trachyspermum ammi seeds | 0.16 g |
| Putranjiva roxburghii seeds | 0.33 g |
| Glycyrrhiza glabra roots | 0.33 g |
| Garcinea cambogia fruits | 0.5 g |
| Ocimum sanctum seeds | 0.06 g |
| Sesamum indicum seeds | 0.33 g |
| Prunus amygdalus gum | 0.1 g |
| Oryza sativa grains | 0.16 g |
| Total | 2.96 g |

The combination of above ingredients was referred to as Formula II (FII). The above ingredients were mixed together to obtain a primary mixture. Pre-formulation studies were carried out for a total of 9 g of primary mixture. The different properties of the mixture are provided in table 5 below:

TABLE 5

| S. No. | Evaluations | Observations |
| --- | --- | --- |
| 1 | Physical appearance | Brownish color |
| 2 | Fineness | 25.20% |
| 3 | Loss on drying | 1% |
| 4 | Loose Bulk density | 0.542 gm/cc |
| 5 | Tapped Bulk density | 0.626 gm/cc |
| 6 | Apparent density | 6.985 gm/cc |
| 7 | True density | 0.922 gm/cc |
| 8 | Hausner's ratio | 0.83 |
| 9 | Carr's Compressibility index | 16.20 |
| 10 | Angle of repose | 27 |

The primary mixture along with 60 mg almond gum as binder, 5 mg of magnesium stearate as the lubricant, and 5 mg of talc as glidant were taken and passed through sieves of size no. 80 to obtain a secondary mixture. After sieving, the secondary mixture was subjected to a final round of mixing in a blender to obtain a powder blend of the herbal ingredients.

The tablets were made by direct compression using the powder blends on a rotating tablet presses using 11×8 mm punch set with appropriate compression pressure and the die cavity was adjusted for required weight. The obtained polyherbal tablets were compressed to 3000 mg tablets. The tablets were evaluated for organoleptic properties, diameter and thickness, weight variation, friability and hardness.

Thickness of the tablet: The tablet thickness was calculated by Vernier calipers. Tablet was put in between two jaws vertically and measured thickness and 6 tablets were used for this test and expressed in mm.

Weight variation test: The average weight was determined by randomly selecting and weighing 20 tablets. Each tablet was also weighed individually. The deviation from the average weight in each case was calculated and expressed as a percentage. Not more than two of the tablets from the sample size deviate from the average weight by a greater percentage and none of the tablets deviate by more than double that percentage.

Percentage friability test: The friability of tablets was determined by Roche friabilator. Percentage of weight loss of 20 tablets randomly selected from each batch tumbled in friability apparatus. After 4 minutes of rotating at 25 rpm, the dust of tablets was removed, and the percentage of weight loss was calculated using the formula.

Percentage friability test=Initial weight–final weight/
initial weight×100

Hardness test: Tablet requires a certain amount of strength or hardness and resistance friability to withstand mechanical shocks of handling in all processes. The hardness of randomly selected 20 tablets of each composition was determined by the Pfizer hardness tester. It was measured in kg/inch$^2$.

Disintegration test: The disintegration time of tablets was determined using the digital microprocessor based disintegration test apparatus (basket rack assembly, Lab India). One tablet was introduced into each tube and added a disc. The assembly was suspended in a 1000 mL beaker filled in with water. The volume of water was such that the wires mesh at its highest point (at least 25 mm) below the surface of the water, and at its lower point (at least 25 mm) above the bottom of the beaker. The apparatus was operated and maintained at 37±2° C. The time requires to all tablets to disintegrate and pass through wire mesh was noted.

The results of the test are summarized in the table 6 below.

TABLE 6

| S. No. | Evaluations | Observations |
|---|---|---|
| 1 | Physical appearance | Brownish color |
| 2 | Thickness of tablets | 1.11 ± 0.01 cm |
| 3 | Weight variation | 8000 mg ± 5 mg. per tablet weight |
| 4 | Friability | Within limits |
| 5 | Hardness | 22 kg/cm$^2$ |
| 6 | Disintegration Time required for complete chewing | 5-10 mins. |

Experiment-3: Characterization of the Composition to Study Synergism

The mixture of the powdered solid fractions of the ingredients in composition I and composition II was subjected to Differential scanning calorimetry (DSC) and Fourier-transform infrared spectroscopy (FTIR) studies to evaluate interaction between ingredients.

FIG. 1 illustrates DSC studies graph of composition 1 as shown in table I, according to an embodiment of the disclosure.

The individual components marked in FIG. 1 are shown in table 7:

TABLE 7

| Ingredients | DSC sample codes |
|---|---|
| Cinnamomum zeylyanicum bark | 101 |
| Linum usittatissimum seeds | 103 |
| Vitex agnus-castus berries | 105 |
| Zingiber officinale rhizome | 107 |
| Ocimum sanctum leaves | 109 |
| Emblica officinalis berries | 111 |
| Mentha spicate leaves | 113 |
| Withania somnifera roots | 115 |
| Ferula foetida resin | 117 |
| Cicer arietinum legume | 119 |
| Mixture of all of the above ingredients | 121 |

The DSC of the individual ingredient of the above table revealed that the individual components had endothermic peak at the same melting point. This reveals that the selected herbal ingredients possessing the nearly the same functional groups. Hence, polyherbal composition of Formula I elicits the synergistic pharmacological effect in the treatment of PCOS.

Figure 2:
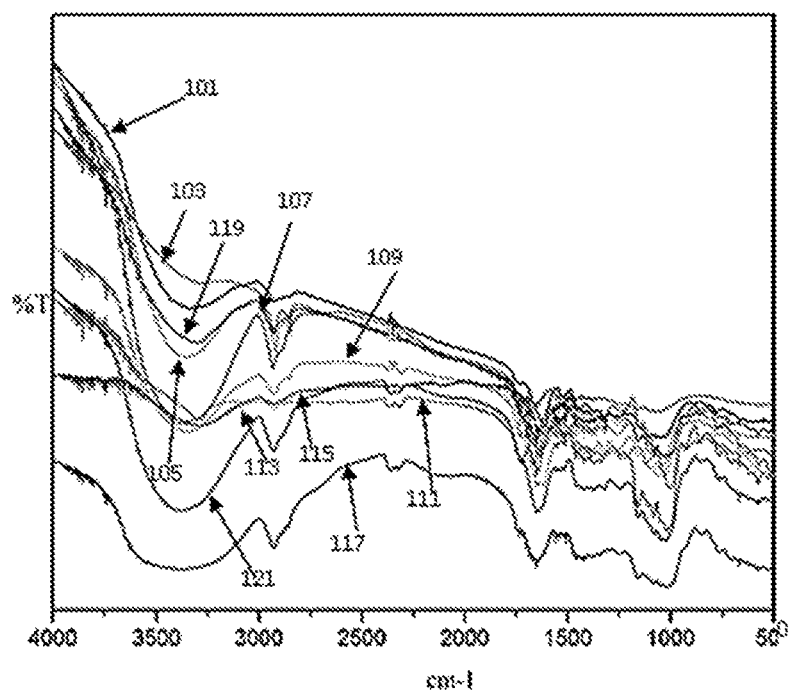
FIG. 2 illustrates FTIR spectroscopy studies of the polyherbal composition FI, according to an embodiment of the disclosure.

FIG. 2 illustrates FTIR studies of composition 1 as shown in table 1, according to an embodiment of the disclosure.

The individual components are marked in FIG. 2 are shown in below in table 8:

TABLE 8

| Ingredients | FTIR sample codes |
|---|---|
| Cinnamomum zeylyanicum bark | 101 |
| Linum usittatissimum seeds | 103 |
| Vitex agnus-castus berries | 105 |
| Zingiber officinale rhizome | 107 |
| Ocimum sanctum leaves | 109 |
| Emblica officinalis berries | 111 |
| Mentha spicate leaves | 113 |
| Withania somnifera roots | 115 |
| Ferula foetida resin | 117 |
| Cicer arietinum legume | 119 |
| Mixture of all of the above ingredients | 121 |

The FTIR studies revealed that all the individual components possess the same functional groups as indicated by the sharp peaks in the functional group region of the IR spectrum as well as the bands in the finger print regions. These indicate that the individual components in the composition provide the synergistic effect towards the treatment of PCOS.

Figure 3:
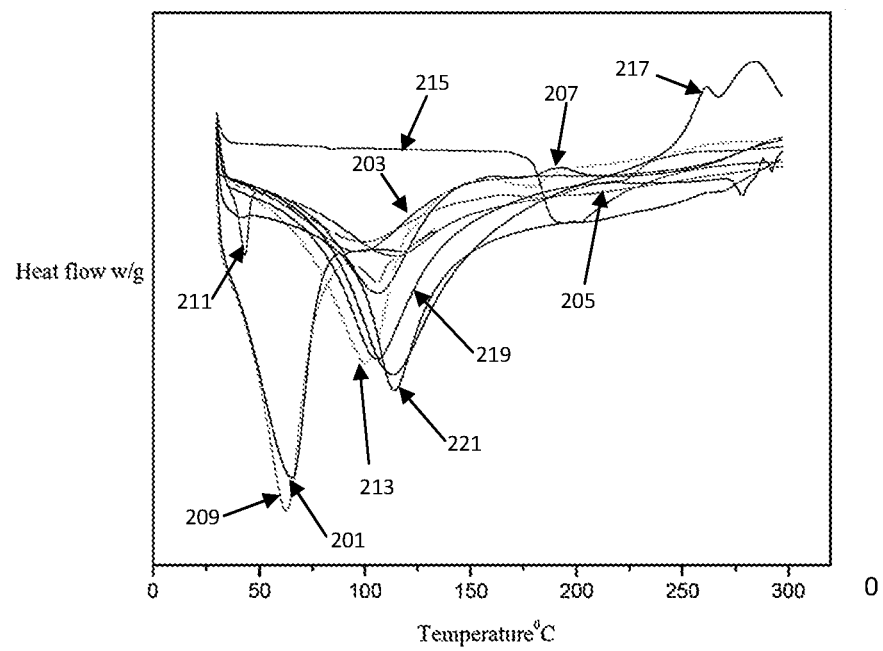
FIG. 3 illustrates DSC spectroscopy studies of the polyherbal composition FII, according to an embodiment of the disclosure.

FIG. 3 illustrates DSC studies graph of composition 2 as shown in table IV, according to an embodiment of the disclosure.

The individual components marked in FIG. 3 are shown in table 9 below:

TABLE 9

| Ingredients | DSC sample codes |
|---|---|
| Trigonella foenum seeds | 201 |
| Tribulus terrestris seeds | 203 |
| Trachyspermum ammi seeds | 205 |
| Putranjiva roxburghii seeds | 207 |
| Glycyrrhiza glabra roots | 209 |
| Garcinea cambogia fruits | 211 |
| Ocimum sanctum seeds | 213 |
| Sesamum indicum seeds | — |
| Prunus amygdalus gum | 217 |
| Oryza sativa grains | 219 |
| Mixture of all ingredients | 221 |

The DSC of the individual ingredient of table 9 revealed that the individual components had endothermic peak at the same melting point. This reveals that the selected herbal ingredients possessing the nearly the same functional groups. Hence, the polyherbal composition II elicits synergistic pharmacological effect in the treatment of PCOS.

Figure 4:
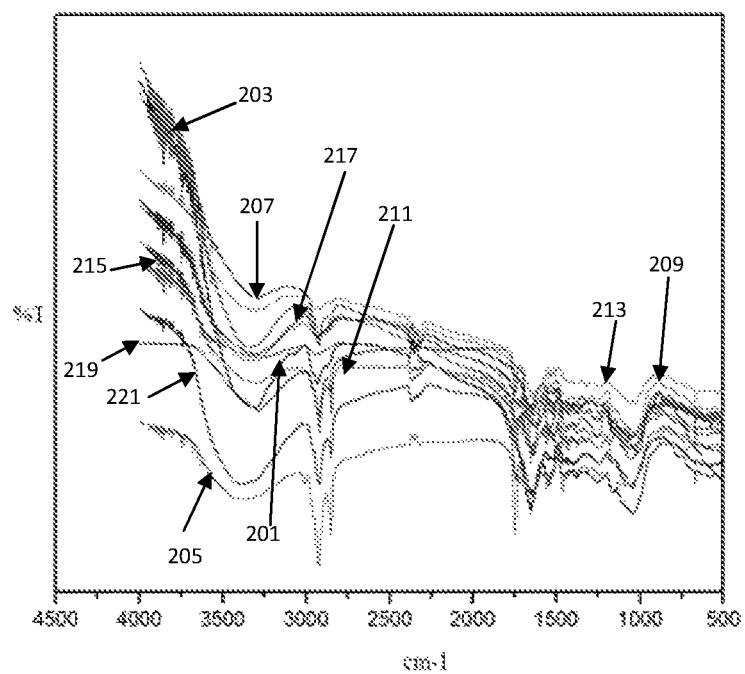
FIG. 4 illustrates FTIR spectroscopy studies of the polyherbal composition FII, according to an embodiment of the disclosure.

FIG. 4 illustrates FTIR studies of composition 2 as shown in table IV, according to an embodiment of the disclosure.

The individual components marked in FIG. 4 are shown below in table 10:

TABLE 10

| Ingredients | FTIR sample codes |
|---|---|
| Trigonella foenum seeds | 201 |
| Tribulus terrestris seeds | 203 |
| Trachyspermum ammi seeds | 205 |
| Putranjiva roxburghii seeds | 207 |

TABLE 10-continued

| Ingredients | FTIR sample codes |
|---|---|
| *Glycyrrhiza glabra* roots | 209 |
| *Garcinea cambogia* fruits | 211 |
| *Ocimum sanctum* seeds | 213 |
| *Sesamum indicum* seeds | 215 |
| *Prunus amygdalus* gum | 217 |
| *Oryza sativa* grains | 219 |
| Mixture of all ingredients | 221 |

The FTIR studies revealed that all the individual components possessing the same functional groups as indicated by the sharp peaks in the functional group region of the IR spectrum as well as the bands in the finger print regions. These indicate that the individual components in the composition 2 provide synergistic effect towards the treatment of PCOS.

Figure 5:
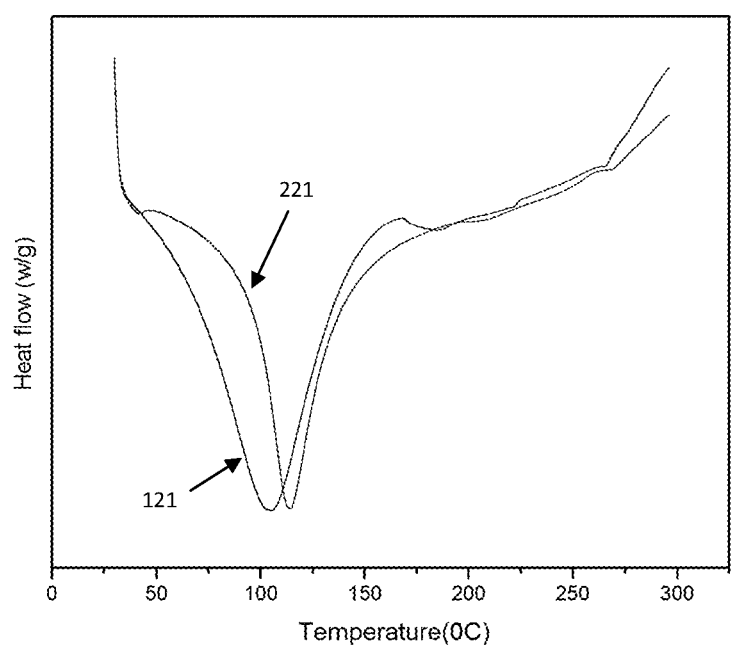
FIG. 5 illustrates comparison of DSC data of composition FI (121) and FII (221), according to an embodiment of the disclosure.

FIG. 5 illustrates comparison of DSC data of composition FI (121) and FII (221), according to an embodiment of the disclosure. The DSC peaks overlay for the composition 1 mixture and composition 2 mixture revealed the endothermic peak at the same melting point temperature indicating that the two compositions containing the components of same functional groups which tend to elicit the similar pharmacological effect as claimed for the treatment of PCOS.

Figure 6:
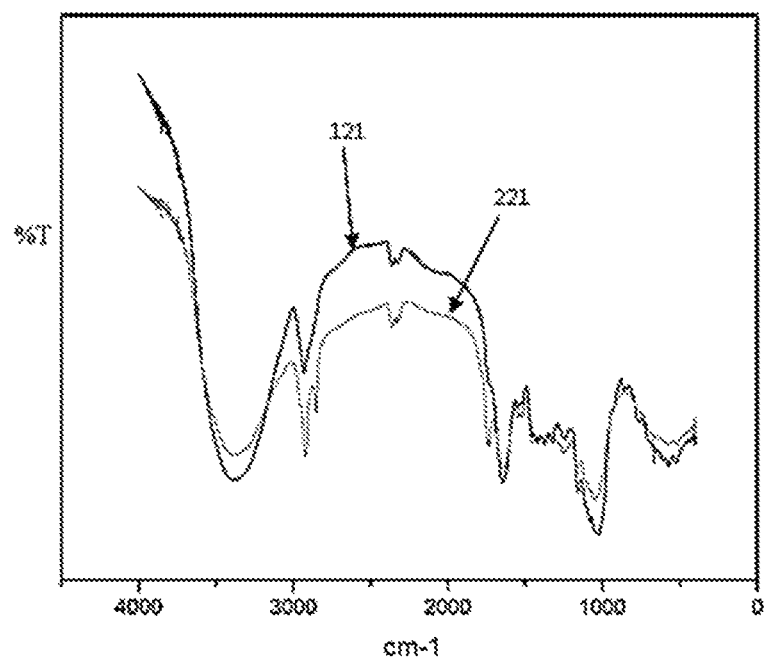
FIG. 6 illustrates comparison of FTIR data of composition FI (121) and FII (221), according to an embodiment of the disclosure.

FIG. 6 illustrates comparison of FTIR data of composition FI (121) and FII (221), according to an embodiment of the disclosure. The FTIR overlay of the composition 1 mixture and composition 2 mixture revealed as the same which indicates that the two composition containing the components of same functional groups which tend to elicit the similar pharmacological effect as claimed for the treatment of PCOS.

Polyherbals selected in the study confer a cumulative effects of the active principles present in each ingredient selected with enhanced efficacy required for desired pharmacological effects and overcome all the concomitant anomalies of PCOS. Hence, the effect produced by the each of the selected ingredients with their effective active principles can exhibit synergistic therapeutic effect with a multi-constituent unit compacted as a single pharmaceutical dosage unit for the effective treatment of PCOS.

The table 11 below provides active principles of each selected ingredients and their role in treating PCOS.

TABLE 11

| S. no. | Ingredients | Active principles | Effect produced |
|---|---|---|---|
| 1. | *Cinnamomum zeylyanicum* bark | Polyphenols and procyanidins. | Regulates insulin stimulated glucose uptake. Regulates menstrual cycle. |
| 2. | *Linum usittatissimum* seeds | Omega-3 fatty acid, dietary Lignans | Normalizes lipid levels. Lignans reduce the excess testosterone and diminish symptoms associated with hyperandrogenism, such as hirsutism. |
| 3. | *Vitex agnus-castus* berries | Monoterpene and beta-caryophyllene | Reduces Prolactin levels. Regulates progesterone levels/ |
| 4. | *Zingiber officinale* rhizome | Zingirone, Gingerol, zingerone etc. | Naturally shrinks ovarian cysts. Normalize menstrual cycle and regulates hormonal levels. |
| 5. | *Ocimum sanctum* leaves | Oleanolic acid, Ursolic acid, Rosmarinic acid, Eugenol, Carvacrol, Linalool, and β-caryophyllene | Controls androgen levels. Also regulates insulin levels and lowers blood sugar level. |
| 6. | *Emblica officinalis* berries | Emblicanin A and B, gallic acid, ellagic acid, ascorbic acid | Regulates blood sugar levels. Also, is rich source of vitamin C with antioxidative effects. |
| 7. | *Mentha spicate* leaves | Carvone, phellandrine, limonene, butyric, caprylic acids | Reduces free and total testosterone levels thereby, reducing the degree of hirsutism. Also, is a rich source of vitamin C with antioxidative effects. |
| 8. | *Withania somnifera* roots | Alkaloids (isopellertierine, anferine), steroidal lactones (withanolides, withaferins) | Regulates adrenal level. Also, has calming effects on the nervous system during periods of mental stress. |
| 9. | *Ferula foetida* resin | Beta sitosterol, Resino tannols 'A' and 'B', ferulic acid, umbelliferone | It balances hormone levels, reduces acne, lowers high blood cholesterol levels. Is rich source of vitamin C with antioxidative effects. Also, has calming effects on the nervous system during periods of stress. |

TABLE 11-continued

| S. no. | Ingredients | Active principles | Effect produced |
|---|---|---|---|
| 10. | *Cicer arietinum* legume | D-chiro Inositol, Ascorbic acid, niacin, tocopherol, pantothenic acid, biotin, pyridoxine, vitamin K | Controls cholesterol levels, Also, has calming effects on the nervous system during periods of stress. |

The table 12 below provides active principles of each selected ingredients and their role in treating PCOS.

TABLE 12

| S. no. | Ingredients | Active principles | Effect produced |
|---|---|---|---|
| 1. | *Trigonella foenum* seeds | Furostanolic saponin | Regulates insulin stimulated glucose uptake. Regulates menstrual cycle. |
| 2. | *Tribulus terrestris* seeds | Dioscin, protodioscin, diosgenin | Normalizes lipid levels. Also, Induces Ovulation induction and reduces symptoms of dysmenorrhea. |
| 3. | *Trachyspermum ammi* seeds | Thymol, para-cymene, γ terpenine, α- and β-pinenes, dipentene, α-terpinene, camphene, myrcene, and α-3-carene | Reduces Prolactin levels. Also, regulates Menstrual cycle, and helps in weight loss. |
| 4. | *Putranjiva roxburghii* seeds | Putranjivin, putranjivoside, beta-sitosterol, beta-amyrin, friedelanol | Naturally shrinks ovarian cysts. Useful in the treatment of sterility. Also, has ant oxidative and hypoglycemic activity. |
| 5. | *Glycyrrhiza glabra* roots | Glycyrrhizin, glycyrrhizinic acid, triterpenoid glycosides (saponins), flavonoids (including liquiritigetol) and isoflavonoids. | Reduce serum testosterone in women with PCOS. Also, has antioxidative effects. |
| 6. | *Garcinea cambogia* fruits | Hydroxyl citric acid | Regulates blood sugar levels and manage insulin levels. Also, aids in weight loss and reduce fat mass. Helps regulating fertility. |
| 7. | *Ocimum sanctum* seeds | Eugenol, nerol, α and α-pinene, camphor and carvacrol | Controls androgen levels. Also regulates insulin levels and lowers blood sugar level. |
| 8. | *Sesamum indicum* seeds | lignans sesamolin, sesamin, pinoresinol and lariciresinol | Regulates adrenal level. Has antioxidative effects. Also, regulates menstrual cycle and cholesterol level. |
| 9. | *Prunus amygdalus* gum | Omega-9 fatty acid, linoleic acid, beta-sitosterol, campesterol, campestanol, stigmasterol and sitostanol, vitamins niacin, riboflavin, thiamine, folate, vitamin B6 and choline. polyphenols and anthocyanins | Has antioxidative effects. Reduces acne. Also, regulates menstrual cycle and cholesterol level. |
| 10 | *Oryza sativa* grains | Inositol (vitamin B8) | Reduces cholesterol levels and aids weight loss. Also, increases ovulation and conception rate. |

Experiment-4: Acute Toxicity Studies on Female Wistar Rats

The polyherbal composition of Formula I and Formula II were then tested for acute toxicity studies in mice. The acute toxicity study was conducted as per OECD guidelines 423.

For this study, six female wistar rats were selected. The rats were randomly selected and were marked to permit individual identification. To allow for acclimatization to the laboratory conditions, the rats were kept in their cages for at least 5 days prior to dosing. The female wistar rats were then divided into groups of two, with three rats in each group. Each rat in the two groups were subjected to overnight fasting prior to administration of the composition. The rats were administered the compositions of FI and FII. Dosing volumes was 1 ml for each rat and the time of dosing was after 4 hours of fasting. Rationale for the selection of the starting dose was as per the OECD guidelines and the acute toxicity dose limit was selected as 2000 mg/kg body weight of the study animals. The dose level for each animal was 0.30 mg/ml of the animal weight 150 g each for FI and 0.36 mg/ml of the animal weight 180 g each for FII.

1% CMC was used as suspension in drug preparation for oral administration. The rats selected for the study were non-Pathogenic. The study group has 6 animals (Each group 3), age of 3 months old of female sex. The housing condition had room temperature of 22±1° C. with 12:12-hour light-dark cycle. The animals were fed with pellet diet and water ad libitum.

All the animals were carefully observed for development of any toxic signs or symptoms at different time intervals of 0, 30 minutes, 1, 2, 4, 6, 8, 12, 24, 48 hrs and then daily for a period of 14 days. The visual observations of mortality, various changes in physical appearance, behavior (salivation, lethargy), reflex response and any injury or illness were observed for 48 hours. The results are given below in table 13.

TABLE 13

| | | FI | | | FII | | |
|---|---|---|---|---|---|---|---|
| S. NO | PARAMETERS | Animal I | Animal II | Animal III | Animal IV | Animal V | Animal VI |
| 01 | AGITATION | x | x | x | x | x | x |
| 02 | CONVULSION | x | x | x | x | x | x |
| 03 | VOCAL | x | x | x | x | x | x |
| 04 | FREMITUS | x | x | x | x | x | x |
| 05 | STEREOTYPED MOVEMENTS | x | x | x | x | x | x |
| 06 | TOUCH RESPONSE | ✓ | ✓ | ✓ | ✓ | ✓ | ✓ |
| 07 | SALIVATION | x | x | x | x | x | x |
| 08 | TACHYCARDIA | x | x | x | x | x | x |
| 09 | TREMORS | x | x | x | x | x | x |
| 10 | ABDOMINAL WRITHING | x | x | x | x | x | x |
| 11 | STRETCH | x | x | x | x | x | x |
| 12 | PROSIS | x | x | x | x | x | x |
| 13 | SLEEPINESS | ✓ | ✓ | ✓ | ✓ | ✓ | ✓ |
| 14 | HINDIQUARTER | x | x | x | x | x | x |
| 15 | CYANOSIS | x | x | x | x | x | x |
| 16 | DEFEACTION | N | N | N | N | N | N |
| 17 | DIARRHOEA | x | x | x | x | x | x |
| 18 | TEARING | x | x | x | x | x | x |
| 19 | URINATION | N | N | N | N | N | N |
| 20 | PILOERECTION | x | x | x | x | x | x |
| 21 | NO. OF DEATH | Nil | Nil | Nil | Nil | Nil | Nil |

No side effects of the administered composition were observed in the female wistar rats The test drug-treated Wistar rats showed normal responses in a period of four hours and did not shown any signs of toxicity. There were no significant changes in the body weight, food and water intake.

The female wistar rats were then tested to observe any acute toxicity effects of the composition for which the following studies were carried out:

Hematological Study:

The animals were anesthetized by isoflurane and the blood samples were collected into EDTA containing tubes for hematological parameters. The hematological parameters of the tested wistar rats three in each group of FI and FII in comparison with control group are shown in table 14 below.

TABLE 14

| S. NO. | HEMATO-LOGICAL PARAMETER | CONTROL | FORMULA - I | FORMULA - II |
|---|---|---|---|---|
| 1) | Hb Count (gm) | ns 10.86 ± 0.04 | ns 9.6 ± 0.6 | ns 12.0 ± 0.2 |
| 2) | Hb gm % (%) | ns 74.89 ± 0.2 | ns 66.06 ± 4.14 | ns 82.75 ± 1.38 |
| 3) | RBC (millions/ml) | ns 8.6 ± 0.2 | ns 9.49 ± 0.185 | ns 7.01 ± 0.18 |
| 4) | WBC (c/mm) | ns 11.8 ± 1.4 | ns 13.77 ± 1.67 | ns 10.52 ± 0.57 |

Values are expressed as the mean ± SEM (N = 3, for each group, female rats);
$p > 0.05$ using student T-test (unpaired);
ns Not significant.

Supplementation of female Wistar rats with compositions of Formula I or Formula II did not affect the HB count, RBC count or the WBC count of the animal. There were no changes in the haematological parameters and vital organ weight changes.

Body Mass Index Measurement of the Study Animals:

The body weight changes were measured for each animal at an interval of $7^{th}$ and $14^{th}$ day in comparison with the control group and the average of the values were observed for the animals which are shown in table 15 below.

TABLE 15

| S. NO | ANIMAL OBSERVATION | CONTROL | FORMULA - I Body Weight (gm) | FORMULA - II Body Weight (gm) |
|---|---|---|---|---|
| 1) | 0 Day | 158 | 151 | 181 |
| 2) | $7^{th}$ Day | 162 | 153 | 165 |
| 3) | $14^{th}$ Day | 164 | 157 | 175 |

Values are expressed as the mean ± SEM (N = 1, for each group, female ns rats);
$p > 0.05$ using Student T-test (unpaired);
ns Not significant.

The animals showed no signs of toxicity including mortality, nature, severity, and duration of effects. The body weight changes indicated slight decrease in body weight after single dose administration in the first week. However, the rats regained its body weight after a week of administration of both the compositions. Individual weights of animals at the day of dosing, in weekly intervals, were illustrated in table 15.

Evaluation of Food & Water Intake Parameter:

For this, the food and water intake were measured for one animal in each group at an interval of 7th and 14th day in comparison with the control group and the average of the values were observed for the animals which are shown in table 16 below. Until 14 days the animal showed no mortality.

TABLE 16

| | | CONTROL | | FORMULA - I | | FORMULA - II | |
|---|---|---|---|---|---|---|---|
| S. NO | ANIMALS | FOOD (gm) | WATER (ml) | FOOD (gm) | WATER (ml) | FOOD (gm) | WATER (ml) |
| 1) | $7^{th}$ Day | 13 | 30 | 14 | 42 | 11 | 24 |
| 2) | $14^{th}$ Day | 15 | 25 | 16 | 23 | 16 | 22 |

The animals showed no signs of toxicity including mortality, nature, severity, and duration of effects. The food intake after the administration of FI and FII remain unaltered. However, due to marginal increase in the metabolic rate a slight increase in the water intake were observed.

Vital Organs Measurements of the Study Animals:

For this, the two animal from each group not considered for water intake were taken for sacrifice and measured for vitality of organs. The vital organs namely the liver, heart, spleen, lung, uterus, ovaries and kidney, were carefully excised and weighed. These organs were preserved in a fixation medium of 10% buffered formalin for histopathological study. The vital organs heart, kidney, uterus, ovary, stomach, lungs, liver were observed in the study which revealed that there was no toxicity observed for the vital organs. The results are summarized in the table 17, depicting evaluation of relative organ weight after administration of compositions of FI & FII.

TABLE 17

| S. NO | ANIMAL OBSERVATION | CONTROL (Body weight - 159 g) | FORMULA - I (Body weight - 150 g) Organ Weight (gms) | FORMULA - II (Body weight - 180 g) Organ Weight (gms) |
|---|---|---|---|---|
| 1) | HEART | ns<br>0.29 ± 0.02 | ns<br>0.31 ± 0.03 | ns<br>0.26 ± 0.01 |
| 2) | LIVER | ns<br>4.11 ± 0.13 | ns<br>4.83 ± 0.23 | ns<br>3.36 ± 0.31 |
| 3) | KIDNEY | ns<br>0.63 ± 0.01 | ns<br>0.70 ± 0.03 | ns<br>0.57 ± 0.07 |
| 4) | LUNGS | ns<br>0.76 ± 0.23 | ns<br>0.9 ± 0.10 | ns<br>0.48 ± 0.04 |
| 5) | STOMACH | ns<br>0.71 ± 0.03 | ns<br>0.80 ± 0.07 | ns<br>0.50 ± 0.05 |
| 6) | UTERUS | ns<br>0.27 ± 0.01 | ns<br>0.30 ± 0.03 | ns<br>0.22 ± 0.0 |
| 7) | OVARY | ns<br>0.06 ± 0.45 | ns<br>0.07 ± 0.01 | ns<br>0.04 ± 0.005 |

Values are expressed as the mean ± SEM (N = 2, for each group, female rats);
$p > 0.05$ using Student T-test (unpaired);
ns Not significant.
Relative organ weight was calculated as (organ weight (g)/body weight of animal on sacrifice day (g)) × 100.

No sign of toxicity was observed up to 2000 mg/kg body weight. This provided that the compositions of FI & FII were proved to be non-toxic Therefore, it is concluded that the administration of compositions of formula I & II are safest & has no adverse effect on growth-related and hematological parameters. It is also inferred that compositions of formula I & II being safe at a higher limit dose, and indicative of very high LD50 value. The list of plants selected and the composition of individual plants in the compositions with its important phytomolecule are responsible for the activity. Hence, it can be recommended as a safe product to replace the synthetic drug in PCOS and used for supplementation in the basal diet for regular usage.

TECHNICAL ADVANCEMENTS

The present disclosure described herein above has several technical advantages including, but not limited to, the realization of:

a polyherbal compositions for preventing and alleviating polycystic ovary syndrome;

and a polyherbal compositions which has no side effects;

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation

The invention claimed is:

1. A polyherbal composition for preventing and alleviating polycystic ovary syndrome, the composition comprising:
   powdered *Trigonella foenum* seeds as an insulin regulator, in an amount ranging from 15% w/w to 25% w/w;
   powdered *Garcinea cambogia* fruits as a blood sugar regulator, in an amount ranging from 15% w/w to 20% w/w;
   powdered *Tribulus terrestris* seeds as a cholesterol lowering agent, in an amount ranging from 10% w/w to 15% w/w;

powdered *Trachyspermum ammi* seeds as a prolactin regulator, in an amount ranging from 3% w/w to 7% w/w;

powdered *Putranjiva roxburghii* seeds as a cyst shrinking component, in an amount ranging from 10% w/w to 15% w/w;

a mixture of powdered *Ocimum sanctum* seeds and powdered *Glycyrrhiza glabra* roots as an androgen regulator, in an amount ranging from 2% w/w to 12% w/w;

powdered *Sesamum indicum* seeds as an adrenal gland regulator, in an amount ranging from 10% w/w to 15% w/w;

powdered *Oryza sativa* grains as an inositol containing component, in an amount ranging from 1% w/w to 10% w/w;

powdered *Prunus amygdalus* gum as a binder, in an amount ranging from 1% w/w to 5% w/w; and a pharmaceutically acceptable excipient in amount ranging from 1% w/w to 5% w/w;

wherein the polyherbal composition is in the form selected from the group consisting of a chewable lozenge tablet, a sugar coated oral tablet, a polymer film coated tablet and gelatin encapsulated tablet, wherein the chewable lozenge tablet is prepared by a process selected from a wet granulation process, a dry granulation process, a direct compression process and/or combinations thereof.

2. The polyherbal composition of claim 1, wherein the composition comprises 15% w/w to 25% w/w of powdered *Cinnamomum zeylyanicum* bark; 10% w/w to 15% w/w of powdered *Linum usittatissimum* seeds; 3% w/w to 7% w/w of powdered *Vitex agnus-castus* berries, 10% w/w to 15% w/w of powdered *Zingiber officinale* rhizome; 2% w/w to 12% w/w of powdered *Ocimum sanctum* leaves; 15% w/w to 20% w/w of powdered *Emblica officinalis* berries, 2% w/w to 12% w/w of powdered *Mentha spicate* leaves; 10% w/w to 15% w/w of powdered *Withania somnifera* roots; 11% w/w to 5% w/w of powdered *Ferula foetida* resin; and 1% w/w to 10% w/w of powdered *Cicer arietinum* legume.

3. The polyherbal composition of claim 1, wherein the pharmaceutically acceptable excipient is selected from the group consisting of at least one of an edible carrier, a binder, a diluent, a disintegrating agent, a coloring agent, a stabilizer, an emulsifier, a film forming agent, a plasticizer, a wetting agent, a thickener, a lubricant, a preservative agent, a sweetening agent, and a flavoring agent.

4. The polyherbal composition of claim 1, wherein the sugar oral tablet is prepared by sealing, sub coating, smoothing syruping, coloring, polishing and printing.

5. The polyherbal composition of claim 1, wherein polymer film coated tablet is formed from an enteric film forming polymer, a non-enteric film forming polymer and/or combinations thereof.

6. The polyherbal composition of claim 1, wherein the gelatin encapsulated tablet is a hard gelatin capsule or a soft gelatin capsule.

7. A method of treating polycystic ovary syndrome in human females comprising administering an effective amount of the composition of claim 1.

8. The method of treatment of claim 7, wherein the effective amount is in the range of 1 g to 3 g of the composition administered two times to three times in a day.

* * * * *